(12) United States Patent
Hotaling

(10) Patent No.: US 9,247,904 B2
(45) Date of Patent: Feb. 2, 2016

(54) APPARATUS FOR NONINVASIVELY MEASURING CORPORAL HEMODYNAMIC AND MECHANICAL PARAMETERS FOR THE DIAGNOSIS OF SEXUAL FUNCTION IN MEN AND WOMEN

(71) Applicant: Andro360 LLC, Seattle, WA (US)

(72) Inventor: James M. Hotaling, Chicago, IL (US)

(73) Assignee: ANDRO360 LLC, Seattle, WA (US)

( * ) Notice: Subject to any disclaimer, the term of this patent is extended or adjusted under 35 U.S.C. 154(b) by 113 days.

(21) Appl. No.: 14/102,504

(22) Filed: Dec. 11, 2013

(65) Prior Publication Data

US 2014/0171767 A1 Jun. 19, 2014

Related U.S. Application Data

(60) Provisional application No. 61/737,107, filed on Dec. 14, 2012.

(51) Int. Cl.
| | | |
|---|---|---|
| A61F 5/00 | (2006.01) |
| A61B 5/00 | (2006.01) |
| A61B 8/06 | (2006.01) |
| A61B 8/00 | (2006.01) |
| A61B 5/026 | (2006.01) |
| A61B 5/01 | (2006.01) |
| A61B 5/107 | (2006.01) |
| A61B 5/11 | (2006.01) |
| A61B 5/1455 | (2006.01) |
| A61B 8/08 | (2006.01) |

(52) U.S. Cl.
CPC ............... *A61B 5/4393* (2013.01); *A61B 8/06* (2013.01); *A61B 8/4227* (2013.01); *A61B 5/0022* (2013.01); *A61B 5/0053* (2013.01); *A61B 5/01* (2013.01); *A61B 5/026* (2013.01); *A61B 5/1072* (2013.01); *A61B 5/1107* (2013.01); *A61B 5/1121* (2013.01); *A61B 5/14551* (2013.01); *A61B 8/485* (2013.01); *A61B 8/488* (2013.01)

(58) Field of Classification Search
CPC ............ A61B 5/00; A61B 5/026; A61B 5/43; A61B 5/4375; A61B 5/4393
USPC .............................................. 600/38–41, 587
See application file for complete search history.

(56) References Cited

U.S. PATENT DOCUMENTS

| | | | | |
|---|---|---|---|---|
| 4,911,176 | A * | 3/1990 | Timm et al. ................... | 600/587 |
| 4,928,706 | A * | 5/1990 | Trick ............................. | 600/587 |
| 6,251,076 | B1 * | 6/2001 | Hovland et al. ............... | 600/454 |
| 2010/0016759 | A1 * | 1/2010 | Lavoisier ...................... | 600/587 |

* cited by examiner

*Primary Examiner* — John Lacyk
(74) *Attorney, Agent, or Firm* — Richards Patent Law P.C.

(57) ABSTRACT

A system and device for measuring sexual function includes an adjustable ring forming an opening to receive a penis, at least one diagnostic sensor positioned on an inner surface of the adjustable ring, wherein the ring automatically couples the diagnostic sensor to the penis throughout a range of ring diameters, and a microcontroller in communication with the at least one diagnostic sensor. The at least one diagnostic sensor measures data during sexual activity and communicates the data to the microcontroller. In fact, in an example, the device is configured to be worn by a user during sexual activity.

18 Claims, 8 Drawing Sheets

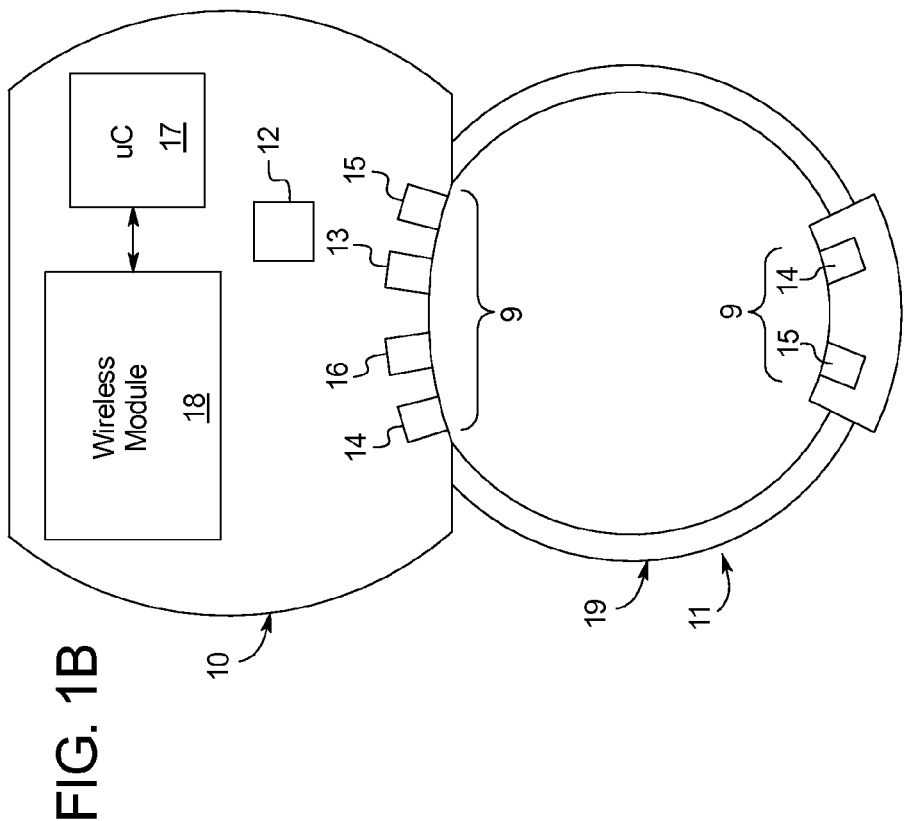
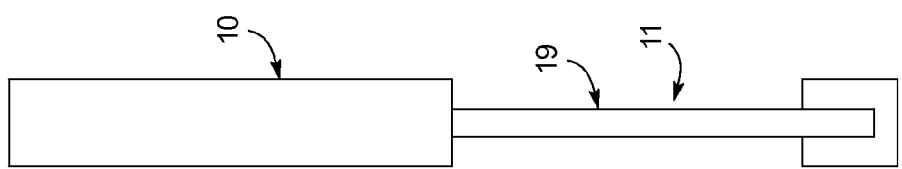

APPARATUS FOR NONINVASIVELY MEASURING CORPORAL HEMODYNAMIC AND MECHANICAL PARAMETERS FOR THE DIAGNOSIS OF SEXUAL FUNCTION IN MEN AND WOMEN

CROSS-REFERENCE TO RELATED APPLICATIONS

This application incorporates by reference and claims priority to U.S. Provisional Application No. 61/737,107 filed on Dec. 14, 2012.

BACKGROUND OF THE INVENTION

The present invention relates generally to a medical device for measuring sexual function.

Sexual dysfunction (SD) is defined as the difficulty experienced by an individual or a couple during any stage of a normal sexual activity. Erectile dysfunction (ED) can be defined as the inability to obtain and/or maintain a penile erection sufficient for intercourse. ED may result from arterial, cavernosal/venous, neurologic, hormonal, autonomic, pharmacologic and/or psychological factors. SD and ED are prevalent conditions and are associated with poorer quality of life metrics. Furthermore, secondary analysis from the Prostate Cancer Prevention Trial (PCPT) trial showed that men with ED without a history of cardiovascular disease were at 45% increased risk of having a subsequent cardiovascular event, and this finding has been confirmed in many other studies (Thompson JAMA 2005).

The diagnosis of SD and ED relies in large part on patient-derived history and self-administered questionnaires. There are a few clinical diagnostic instruments used in the diagnostic evaluation of erectile dysfunction, but they are not commonly used due to expense, patient discomfort, lack of useful diagnostic information yielded, and/or invasiveness.

For instance, large epidemiological studies on the prevalence and predictors of sexual dysfunction have relied on patient-reported questionnaires and not on diagnostic instruments (Laumann et al. JAMA 1999; 281(6):537-544) (Burke J P et al J Urol 2007 April; 177(4):1438-42). The prevalence and predictors of sexual dysfunction due to medical-related treatments, such as radiation or surgical treatment for prostate cancer, is of particular interest. These studies have relied on demographic information and patient-reported measures of sexual health-related quality of life domains to assess the impact of treatment to sexual function (Kuban et al. JAMA 2011; 306(11):1205-1214) (Steineck et al. NEJM 2002; 347 (11):790-6). Finally, large randomized, controlled trials require metrics to assess whether treatment improves erectile function. The major randomized control trials have used pre-treatment and post-treatment diaries, or questionnaires such as the International Index of Erectile Function (Goldstein et al. NEJM 1998; 338:1397-1404) (Padma-Nathan et al. NEJM 1997; 336:1-7) (Brock et al. J Urol 2002 October; 168(4 Pt 1): 1332-6).

Thus, while patient-reported symptoms are a key element of overall sexual heath, there is a need for objective and reproducible data on sexual function. Such data would allow for better characterization of the prevalence and predictors of sexual dysfunction, enhance the understanding of treatment-related effects on erectile function, improve the ability to accurately compare the effectiveness of treatments for ED, and offer an objective tool for assessing increased risk of cardiovascular disease.

Currently available diagnostic tools and instruments to assess for SD and ED are limited by the conditions required to obtain data, invasiveness, and by the amount of useful information they provide, which are all reasons for why they have not been utilized in major studies. The best objective test for ED is performed by intracavernosal injection of a vasoactive substance into the penis while the patient is at a doctor's office, followed by measuring the velocities of the blood flow in the cavernosal arteries within the penis using a hand-held Doppler ultrasound device. This test is invasive, does not provide relevant situational (in vivo) data, and is not frequently a part of an ED work-up as it rarely changes clinical management. There is no commonly accepted work-up of SD or assessment of mechanical or hemodynamic parameters of the clitoris in females beyond patient interviews and questionnaires.

Another technology presently used to measure penile blood flow is the color duplex ultrasound in hand-held devices. This method utilizes high resolution, real-time ultrasonography and color-pulsed Doppler to visualize arterial and venous flow. Hand-held ultrasound measurement devices are limited by the angle of incidence and user experience, which can cause variability and imprecision inherent in a hand-held device. Other inventions address this method by placing the transducer on an apparatus that fits onto the penis.

An apparatus for penile hemodynamic monitoring using ultrasound typically uses an ultrasound generator, display, and adjustable clamp around the penis, such as those disclosed in U.S. Pat. Nos. 5,931,783, 6,221,021, 6,814,702, and 5,947,901, and U.S. Patent Application Pub. No. 2007/0129635. The user applies an ultrasound coupling gel to the surface of the penis, and places the apparatus around the penis. The user holds the apparatus in place while ultrasound energy is delivered to the penis. The energy is able to monitor and/or stimulate hemodynamic activity such as blood flow to the penis. However, the apparatus is bulky and requires the user to hold the apparatus in place. It also requires frequent adjustment to allow for adequate coupling of the sensors to the skin. For these reasons, this limits when and where the apparatus can be used, and prohibits real-time data collection during intercourse, which would most accurately represent the patient's disease, which is private in nature. In summary, this apparatus cannot provide true in vivo data of how an erection performs during sexual intercourse.

A smaller device has been described in U.S. Pat. No. 6,251,076 that includes fixed transducers aligned for Doppler ultrasound measurements of the cavernosal arteries. This is an office-based device that is secured to the penis with a fixing device. The device can be used with vasodilating agents to measure peak systolic and end diastolic velocities and resistive indices. This device, while smaller, is still bulky, has rigid components, and requires a supervising physician to operate and interpret the information. It also provides pulse oximetry data based on the transducers but if these are not placed precisely over the arteries, it cannot obtain any useful information. Again, this apparatus cannot provide true in vivo data of how an erection performs during sexual intercourse.

Another apparatus to measure penile rigidity and arterial-venous flows disclosed in U.S. Pat. No. 4,747,415 and U.S. Patent Application Publication No. 2010/0016759 uses pressure transducers to measure intracavernous pressure and pulse pressure of the penis. The sensor is paced around the penis and the measurements are collected during both day and night. Similar to a blood pressure cuff placed on the arm, the device comprises a cuff with a band and velcro strap. It can only measure the radial rigidity of the penis, and requires an experienced user to operate. It does not measure penile axial buckling forces. This apparatus also cannot provide true in vivo data of how an erection performs during sexual intercourse.

Another apparatus is the Nocturnal Penile Tumescence and Rigidity (NPTR) monitoring device disclosed in U.S. Pat. Nos. 4,606,353 and 6,162,188, which contains two loops placed at the base of the penis and near the end of the penis that measure axial rigidity. This device is used to distinguish between organic and psychogenic causes of erectile dysfunction. Patients with organic dysfunction will not have erections at night. Patients with psychogenic causes of erectile dysfunction are able to have erections at night. The treatment of erectile dysfunction in each group is different. While this data may be beneficial for a select subset of patients, the data from this apparatus is limited and may not be reproducible while the user is awake and during attempted sexual intercourse. Measurements are obtained overnight while the user is asleep using an automated, portable device. The NPTR device includes a sensor for photoplethysmography. It only measures the radial rigidity of the penis, and requires an experienced user to operate. It does not measure penile axial buckling forces. The device is cumbersome and may require the patient to stay overnight at a monitored facility. It also does not provide in vivo data of how an erection performs during sexual intercourse.

Another apparatus is the Rigidometer disclosed in U.S. Patent Application Pub. No. 2010/0217150, which consists of an instrument that measures penile rigidity by pressing the instrument against the penis for a predetermined period. A visual digital readout indicates the cavernosal pressure of the penis. The penis is placed within a separate instrument while the penis is erect. This provides data on penile axial buckling forces but does not measure the radial rigidity of the penis.

Another apparatus disclosed in U.S. Pat. No. 7,390,297 attempts to relieve erectile dysfunction by having a restricting band at the base of the penis to prevent blood from leaving the penis. The device has a temperature gauge that measures the temperature of the scan, and the results can be interpreted visually while worn and monitored. The temperature is displayed using a thermochromic surface, which changes color based on contact with a surface. This device provides no objective numerical data. Further, these devices are not frequently used as they cause painful ischemia that is not relieved by the fixed source of blood flow obstruction, in this case the ring. Although the thermochromic surface attempts to give some feedback, this is an open feedback loop that relies on the user taking off the device as a crude binary on/off modulation.

Another apparatus disclosed in EP1054626 measures changes in clitoral, vaginal-artery, and/or vaginal-capillary blood flow, clitoral engorgement, and bioimpedance. It includes an ultrasound transducer, oximeter probe near the vaginal wall, audio feedback, pH measurement, control electronics, with the housing to be placed within the vagina. The major limitation of this device is that it is bulky and cannot be used during penetrative intercourse.

None of the above devices are able to adequately and objectively measure penile or clitoral rigidity, blood flow, and temperature during the acts of masturbation or coitus. In addition, none of the disclosed devices provide real time, in vivo data to the user, health care professionals, or researchers. The above devices are invasive, cumbersome, and bulky for the patient. Further, a majority of the above devices require trained, experienced personnel to place, position, and operate. In addition, the above devices only provide a partial characterization of the penile/clitoral erection, and thus, multiple devices and simulations must be required to obtain adequate objective data. All of the devices have multiple wired connections to the apparatus that is placed on the penis, which adds to the bulkiness and invasiveness of the instrument. Furthermore, none of these devices have the ability to improve erectile function through a closed feedback loop providing a non-painful erection that can be used during coitus. Likewise, none of the devices provide a back-end mechanism for transmitting real-time data to another device for analysis or transmitting and de-identifying data for research or clinical use on a large scale.

SUMMARY OF THE INVENTION

To overcome the above and other disadvantages, the purpose of the present invention is to fully evaluate the penis and/or clitoris in the flaccid to erect state using non-invasive methods. The device described herein allows the user to wear an unobtrusive sensor ring around their penis or clitoris during masturbation and intercourse and allows for the capture and analysis of biological data by patients, researchers, and health care professionals.

The present invention is directed towards devices and systems designed to measure blood flow, rigidity, size, movement, and temperature of the penis or clitoris. The present disclosure is directed toward measurement of the penis in the flaccid and erect states, and the process between both states. Embodiments of the system and device may operate and provide measurements taken during intercourse, self-stimulation, after pharmacologic stimulation, in the flaccid state, etc. A miniaturized version of the device may be used to measure the blood flow, rigidity, size, movement, and temperature in the clitoris. Further, through an internal feedback mechanism, the device may be used to help maintain the rigidity and prolong the duration of a penile or clitoral erection without compromising blood supply or causing pain.

In an embodiment, the wearable device includes a power regulation module, a wireless communication module, a microcontroller, and an array of diagnostic sensors. The device may be wirelessly connected to one or more microcontrollers adapted to collect, process, distribute, and store data collected from the device. The sensors in the device may include: one or more ultrasound transducers for monitoring blood flow using Doppler techniques and rigidity using speed of sound measurements; one or more accelerometers for monitoring movement; one or more pulse oximeters for monitoring pulse rate and penile oxygenation level; one or more strain gauges or linear potentiometers for measuring circumference of the penis and radial pressure; one or more temperature sensors, and one or more bend sensors for measuring penile bending/buckling. In some embodiments, the device may also include a constricting ring in communication with the microprocessor, wherein based on the data received, the microcontroller may adjust the tension in the constricting ring so as to maintain or increase the rigidity and/or duration of erections.

The system provided herein may include a microcontroller that may control the sensors and data communication protocols. The system may also include a user-controlled application that is accessible on a user's wirelessly-enabled device (e.g., a smart-phone, tablet, other computer), which processes, stores and displays real-time and processed data collected from the device while also controlling certain actuators on the device. And finally, the system may include an internet-based application capable of receiving, de-identifying, distributing, and storing that data in a manner that may be used for remote diagnosis, research, personal data tracking, psychological counseling, or clinical applications.

In an embodiment the device includes a microprocessor and a battery power module to provide a stable and accurate voltage to the rest of the electronics. The system may also include a wireless data connection module using Wi-Fi, Bluetooth, or other wireless protocols suited to the device's needs, that will allow the data acquired by the device to be streamed to an external receiving device, such as a computer or a smart-phone, where it can be further analyzed. And finally, the device may include an array of sensors to measure different biological and mechanical properties. The device may undergo an initial calibration procedure by the man while his penis is in the flaccid state and then, after this calibration, would be ready to use. It is understood that the device may embody a combination of any one or several of the following components:

a) one or more temperature sensors to measure penile skin temperature in multiple places;

b) one or more accelerometers to measure relative velocity, acceleration and movement of the device which is centered at the base of the penis;

c) one or more continuous-wave ultrasound Doppler transmitter/receiver which provide an assessment of relative blood flow into the cavernosal arteries and out of the sinusoids;

d) one or more ultrasonic transmitters/receivers for determining the speed of sound through the penis/clitoris, used to measure the rigidity of the organ;

e) one or more continuous pulse oximeters (photoplethysmographs), which monitors pulse rate and penile oxygenation based on the color change associated with transitions between oxyhemoglobin and deoxyhemoglobin;

f) one or more strain gauges that measure axial and buckling penile rigidity;

g) one or more strain gauges or other sensors to measure penile circumference and radial rigidity; and h) one or more automated constricting rings that can be adjusted by the device in real-time to increase the rigidity and duration of erections.

In another example, the system includes a user-controlled application that runs on the user's wirelessly-enabled device, such as a smart-phone, tablet, or other computer, and processes, stores, and displays the real-time and processed data collected from the device and also controls certain actuators on the device. An algorithm may be used to obtain a composite erection score, for example a score between 1-100. For example, the validity, accuracy and reliability of the measurements obtained by the device may be assessed across a number of data sets collected and then used to develop a weighted system for determining a reproducible erection score. The software suite may also include an internet-based application and database capable of receiving, de-identifying, distributing, comparing, and storing that data in a manner that may be used for remote diagnosis, research, personal data tracking, psychological counseling, and/or clinical applications.

It is contemplated that there may be three or more sets of models of this device; the first for private, non-medical, self-diagnosis, and/or novelty use; the second for an FDA-approved diagnostic tool for physicians; and the third, as a research model for obtaining novel data on ED in male populations. Further, components of the device may be used to make a similar but smaller device to be placed on or near the female clitoris, as will be recognized by those skilled in the art based on the disclosures provided herein.

In an embodiment, the device for measuring sexual function includes an adjustable ring forming an opening to receive a penis, at least one diagnostic sensor positioned on an inner surface of the adjustable ring, wherein the ring automatically couples the diagnostic sensor to the penis throughout a range of ring diameters, and a microcontroller in communication with the at least one diagnostic sensor. The at least one diagnostic sensor measures data during sexual activity and communicates the data to the microcontroller. In fact, in an example, the device is configured to be worn by a user during sexual activity.

In an example, the least a portion of the adjustable ring is an elastic circumferential gauge, wherein the microcontroller is configured to receive data from the elastic circumferential gauge. The device may further include a power supply module and/or a wireless communication module. In an example, the data includes blood flow data, rigidity data, temperature data, 3-axis acceleration data, or combinations thereof.

In another example, the at least one diagnostic sensor includes a blood flow sensor configured to measure blood flow data. For example, the blood flow sensor includes an ultrasound transducer. In another example, at least one diagnostic sensor includes a rigidity sensor configured to measure penile rigidity data, wherein the rigidity sensor includes an ultrasound transduce. Further, the at least one diagnostic sensor may include a temperature sensor configured to measure penile temperature data of the user. As discussed above, the device may include an accelerometer, wherein the microcontroller is configured to receive 3-axis acceleration data from the accelerometer. In addition, the device may include a pulse oximeter sensor configured to measure oxygenation data, wherein the microcontroller is configured to receive oxygenation data from the pulse oximeter sensor.

In yet another example, the device may include a strain gauge used to determine circumferential data. The microcontroller may adjust the diameter of the adjustable ring based on received data.

The disclosure also provides a system for measuring sexual function comprising a device, wherein the device includes an adjustable ring forming an opening to receive a penis, and at least one diagnostic sensor positioned on an inner surface of the adjustable ring, wherein the adjustable ring automatically couples the diagnostic sensor to the penis throughout a range of ring diameters. The system further includes a microcontroller in communication with the at least one diagnostic sensor, wherein the at least one diagnostic sensor measures data during sexual activity and communicates the data to the microcontroller. The system also includes an application in communication with the microcontroller, wherein the application is configured to analyze the data received from the microcontroller.

In an example, the at least one diagnostic sensor includes a blood flow sensor including an ultrasound transducer. The at least one diagnostic sensor may include a rigidity sensor including an ultrasound transducer. In another example, the device may further include an accelerometer, wherein the microcontroller is configured to receive 3-axis acceleration data from the accelerometer. In addition, the device may further include a strain gauge used to determine circumferential data. Further the microcontroller, in response to the data, is configured to adjust a diameter of the ring to enable a user to maintain an erection during sexual activity.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 1A is a side view of an embodiment of the device disclosed herein.

FIG. 1B is a front view of an embodiment of the device disclosed herein.

DETAILED DESCRIPTION OF INVENTION

Figure 2A:
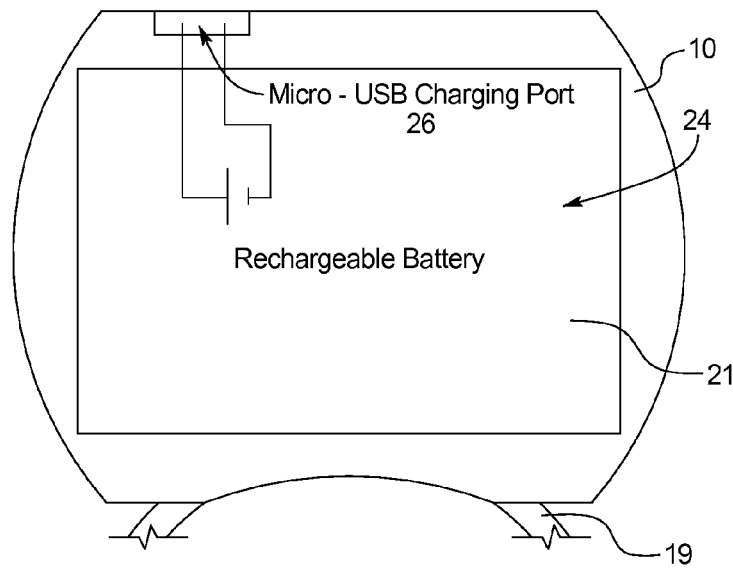
FIG. 2A is a rear view of an embodiment of the housing of the device disclosed herein.

The subject matter provided herein describes a system and device 5 that includes an array of sensors to monitor various biological functions and physical characteristics, namely, sexual functions. The data collected from the device 5 may be wirelessly transmitted to an accompanying microprocessor 17 on a wireless-enabled device such as a smart-phone, tablet, or other computer, wherein the raw data may be collected, stored, processed, and displayed to aid in the diagnosis of various medical problems related to male erectile dysfunction.

Specifically, the present disclosure provides a device 5 for measuring sexual function including an adjustable ring 11 forming an opening to receive a penis, at least one diagnostic sensor 6 positioned on an inner surface 7 of the adjustable ring 11, and a microcontroller 17 in communication with the at least one diagnostic sensor 6, as shown in FIGS. 1A-1B. The ring 11 may automatically couple the diagnostic sensor 6 to the penis throughout a range of ring diameters. The at least one diagnostic sensor 6 measures data during sexual activity and communicates the data to the microcontroller 17. In fact, in an example, the device 5 is configured to be worn by a user before, after, and during sexual activity.

Notwithstanding the depiction in FIGS. 1A-1B, in certain embodiments, the microcontroller 17 is not physically attached to the adjustable ring 11 or the diagnostic sensors 6. Instead, the microcontroller 17 may be housed in a separate electronic device, such as a computer or mobile electronic device (e.g., a smart phone), wherein the diagnostic sensors 6 communicate wirelessly with the microcontroller 17.

The microcontroller 17 may be configured to control and route the data from all the other electronic components of the device 5. The microcontroller 17 may use specific protocols to command and configure the integrated circuits. The device 5 may utilize the microcontroller's 17 built-in analog-to-digital converters (ADC's) or use external ADC's to convert analog DC voltages from some of the sensors 6 to digital values understood by the microcontroller 17. Once the sensor data is obtained, the microcontroller 17 may pre-process it in any way necessary. This includes filtering, timing, storing, scaling, extrapolating and processing raw data to turn it into a form that is useful and small enough to send via wireless protocol to another device where heavier processing may be done. If in the future, wireless protocol data rates or power consumption decrease, this pre-processing step may be eliminated and raw data sent directly.

The diagnostic sensor 6 may be any suitable sensor that is capable of measuring biological and physiological data. For example, as shown in FIG. 1B, the at least one diagnostic sensor 6 may include diagnostic sensors 12-16 and 19: an accelerometer 12, a temperature sensor 13, sound-speed ultrasonic transducer 14a, sound-speed ultrasonic receiver 14b, Doppler ultrasonic transducer 15a, and Doppler ultrasonic receiver 15b, and pulse oximeter 16. These and other various diagnostic sensors 6 will be discussed in more detail below.

Figure 3A:
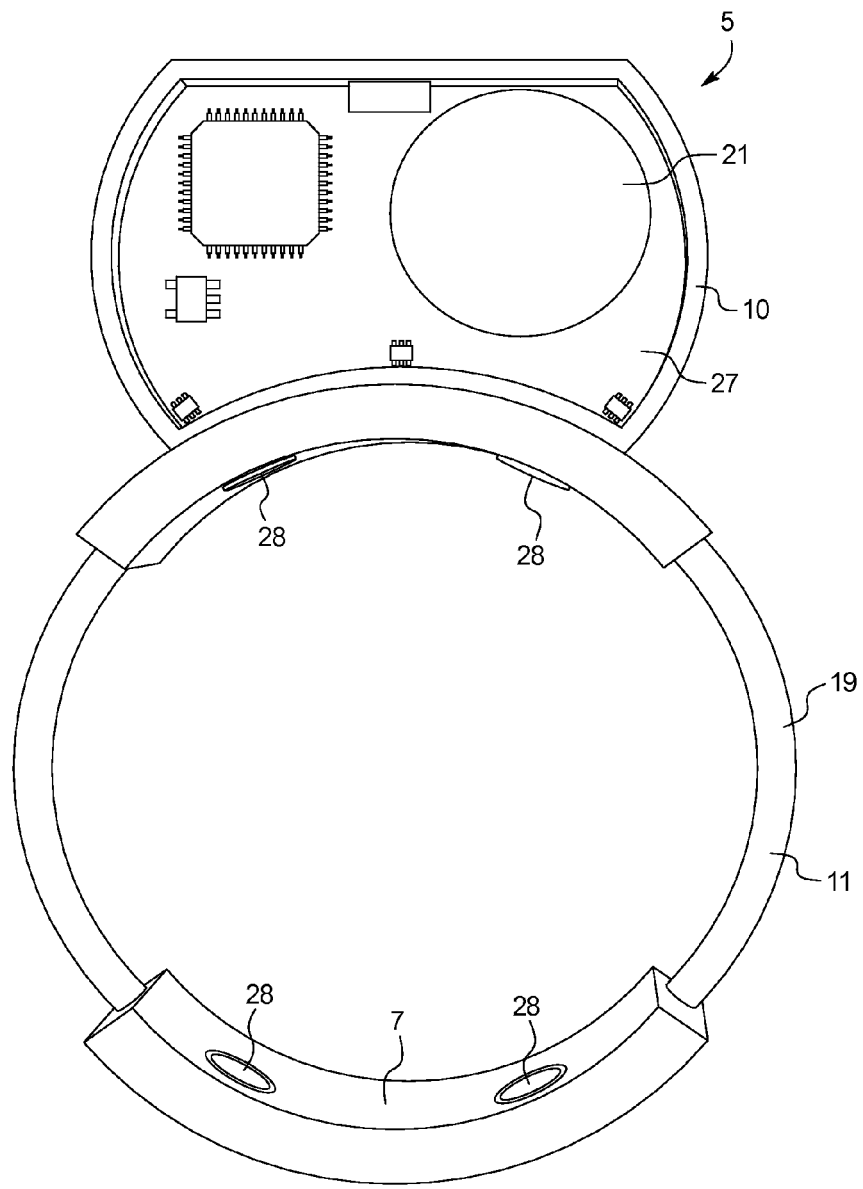
FIG. 3A is a front view of an embodiment of the device disclosed herein, wherein the interior of the housing is shown exposed.
Figure 3B:
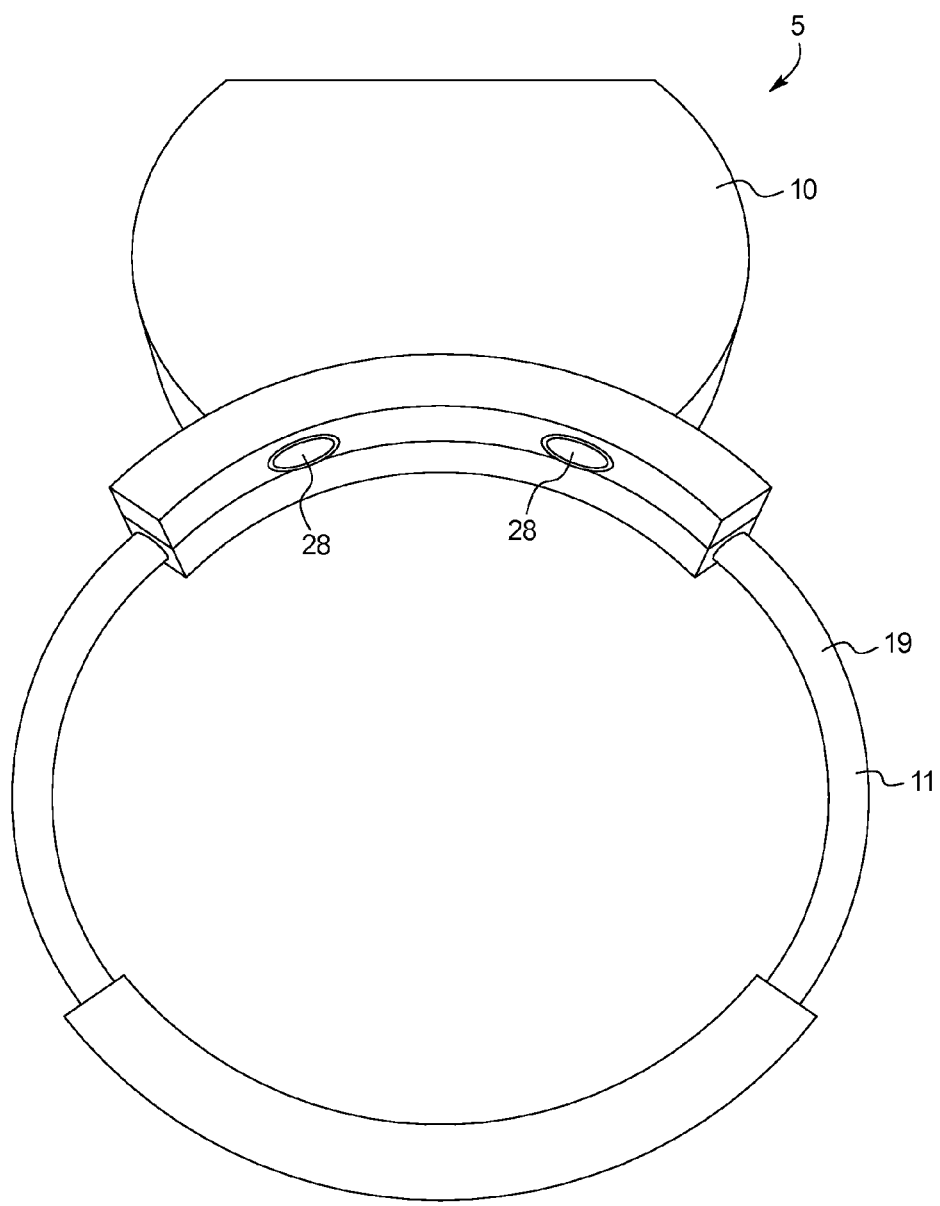
FIG. 3B is a front view of an embodiment of the device disclosed herein, wherein the interior of the housing is not exposed.

The adjustable ring 11 includes an inner surface 7 that is configured to contact the skin of a penis when the device 5 is being worn by a user. Some of the diagnostic sensors, such as the temperature sensor 13, pulse oximeter 16, Doppler ultrasonic transducer 15a, Doppler ultrasonic receiver 15b, sound-speed ultrasonic transducer 14a, and sound-speed ultrasonic receiver 14b, may need to have direct contact with the user's skin. As such, the inner surface 7 may include ports 28 to allow the sensors proper contact in order to obtain accurate measurements, as shown in FIGS. 3A-3B.

The adjustable ring 11 may include an adjustable mechanism for securing the device 5 to the penis. One way this may be accomplished is through the use of an elastic band, which may also serve as a circumferential gauge 19 (e.g., the gauge may be integrated into the elastic/adjustable band). One possible circumferential gauge 19 configuration consists of indium and/or gallium within an elastic, stretchable rubber adjustable ring 11. The circumferential gauge 19 may be in communication with the microcontroller 17 such that the microcontroller 17 is configured to receive data from the circumferential gauge 19.

Another such mechanism for maintaining the device 5 securely and comfortably on the penis is to use a small spring-loaded clamp. In such embodiments, the user may open the clamp, place it over the shaft of the penis and release, securely holding the penis in its grip. The clamp may also include a mechanism to determine how wide the clamp is open, which will in turn give the diameter of the penis. The clamp may be in communication with the microprocessor 17, such that the microprocessor 17 is configured to receive the diameter data from the clamp.

Another mechanism for holding the device 5 securely and comfortably onto the penis is to use an inelastic band attached to a spring-loaded spooling device. The inelastic band is pulled out from the spool, the penis is inserted through the resulting loop, and the band is released. The spool will wind up the remaining band material until the penis shaft is held securely. The spool may also have a mechanism to measure how much the band retracted (i.e., potentiometer), giving a way to measure penis circumference. In such case, the potentiometer may be in communication with the microprocessor 17, such that the microprocessor 17 is configured to receive the band data.

Figure 5:
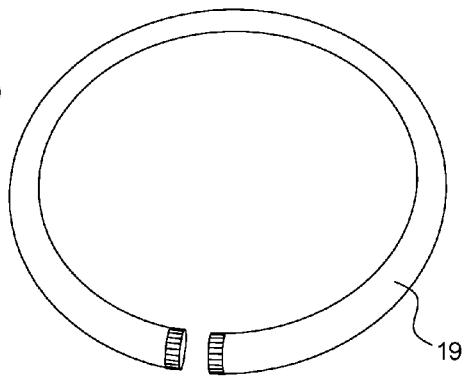
FIG. 5 is front view of an embodiment of a strain gauge.
Figure 6A:
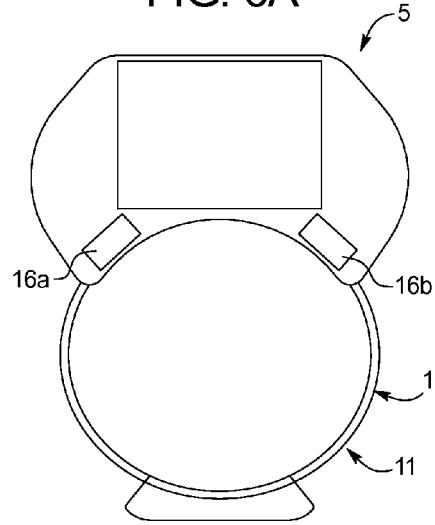
FIG. 6A is a front view of an embodiment of the device disclosed herein.
Figure 6B:
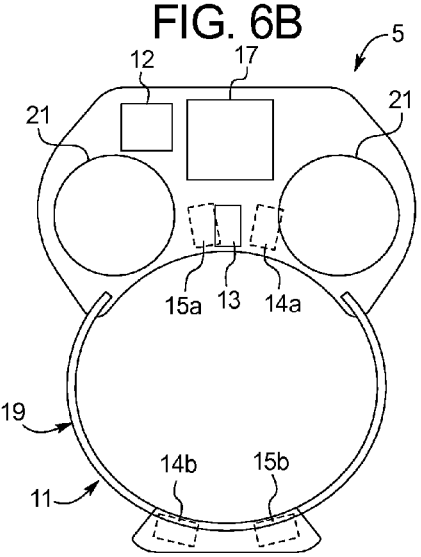
FIG. 6B is a back view of an embodiment of the device disclosed herein.

As discussed above, the adjustable ring 11 may include a circumferential gauge 19 that wraps around the penis shaft and measures changes in penis circumference. The circumferential gauge 19, shown in FIG. 5, may include any type of gauge or mechanism that allows the circumference or diameter of the penis shaft to be measured. In one example, the circumferential gauge 19 may consist of a stretchable rubber tube filled with a mixture of indium and gallium. As the rubber tube expands due to an erection, the liquid metal inside also deforms, changing the resistance value of the circuit when voltage is applied (i.e., a smaller diameter wire has a greater resistance to current passing through than a larger one). This change in resistance can be measured and the corresponding values used to determine the change in circumference and diameter of the penis. If the mechanism for securing the device 5 to the penis uses the small spring-loaded clamp, as described above, then it would be possible to use a small potentiometer to measure the amount the clamp is held open by the penis. This value may be communicated to the microprocessor 17, wherein the value may be used to determine penis diameter.

Another way of measuring circumference data could be a spring-loaded potentiometer connected to an inelastic band or string. During penis expansion and contraction, the inelastic band or string may move the position of the potentiometer, which will result in a changing value of the potentiometer resistance, which can then be used to calculate circumference. Other methods of measuring the circumference of the penis that become available are possibilities for alternate embodiments of the device. The penis circumference values can then be used as reference points for other component tests, as will be recognized by those skilled in the art.

In another example, the adjustable ring 11 may include an electronically actuating constricting mechanism that may constrict the adjustable ring 11 around the shaft of the penis for maintaining an erection at the correct time. In one embodiment, the constricting mechanism may include an air-filled expandable bladder attached to the inner surface of the adjustable ring 11, similar to a blood pressure cuff. In another example, the adjustable ring 11 may include small motors and an inelastic band around the shaft. As will be recognized by those skilled in the art, there are a variety of adjustable rings 11 that may be employed in the device described herein in order to engage a constricting mechanism.

Figure 7:
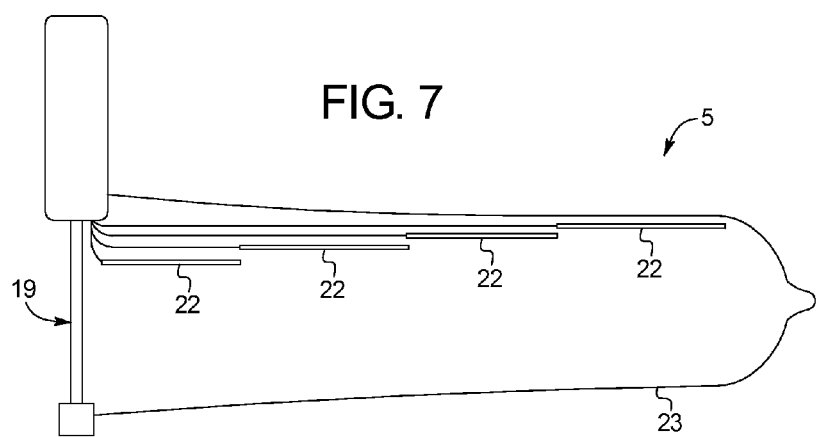
FIG. 7 is side view of a bend sensor as disclosed herein, wherein a condom-like sleeve includes the axial bend sensors.

As shown in FIG. 7, the device 5 may further include a condom-like rubber sleeve 23 that holds axial bend sensors/strain gauges 22 that may be used to measure any penile axial bending. The device 5 may have a mechanism that allows for the secure physical attachment of the rubber sleeve 23, and the reliable electrical attachment of the bend sensors 22. This mechanism will also enable the rubber sleeve 23 to be easily removed and replaced.

In one example, the device 5 may further include a housing 10 that contains electrical and mechanical connections to the diagnostic sensors 6, as shown in, for example, FIGS. 1A-1B and 6A-6B. For example, the housing 10 may include electrical and mechanical connections to diagnostic sensors 6 that reside outside of the housing 10, such as bend gauges 22 in a condom-like rubber sleeve 23 (discussed below), the circumferential gauge 19, and the adjustable ring 11. The housing 10 may contain the microcontroller 17 as shown in FIG. 1B, a power supply module 24 as shown in FIGS. 2A-2B, and a wireless communications module 18 as shown in FIG. 1B.

The housing 10 may be shaped in a way so as to not interfere with a user's sexual activity when the adjustable ring 11 is secured around the shaft of a penis. As shown in FIGS. 3A-3B, the housing 11 is essentially a tab attached to the adjustable ring 11. The housing 10 may be as small, non-intrusive, and lightweight as possible to allow the wearer to act in the same manner as if he were not wearing the device 5, thus, allowing for natural, unencumbered movements and actions. The housing 10 may have a mechanism to allow for the adjustment of an elastic band, such as the circumferential gauge 19, in order to securely attach the device 5 to penises of differing sizes. In an example, the housing 10 may also have a mechanism for replacing the band or clamp, for hygienic reasons or in other situations requiring replacement.

Figure 2B:
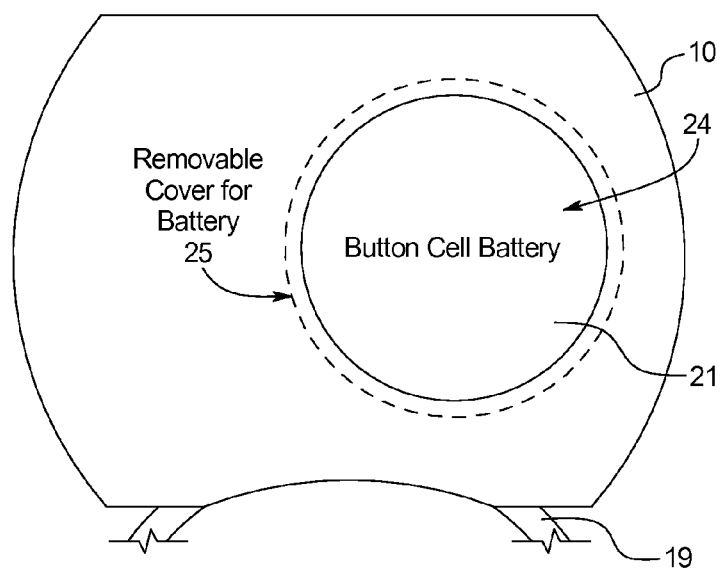
FIG. 2B is a rear view of an embodiment of the housing of the device disclosed herein.
Figure 4A:
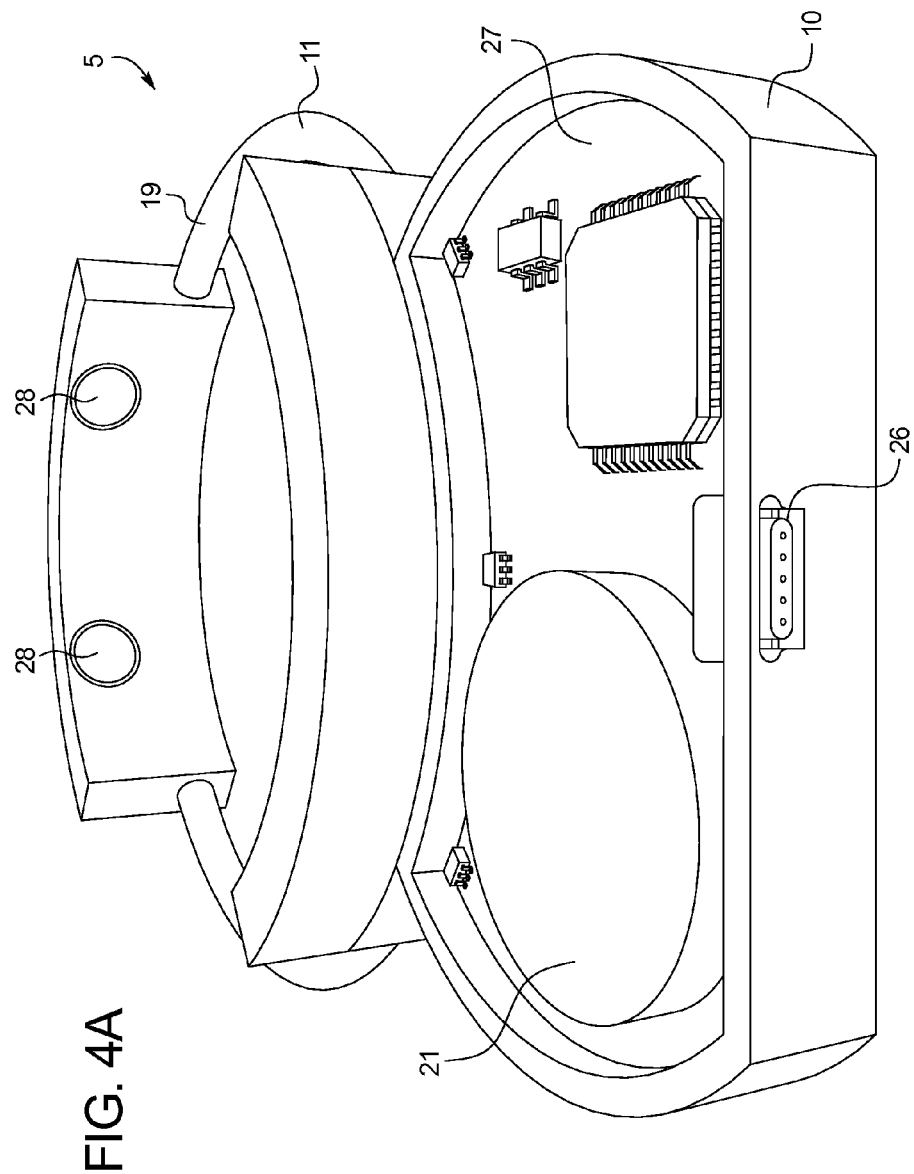
FIG. 4A is a top view of an embodiment of the device disclosed herein, wherein the interior of the housing is exposed.
Figure 4B:
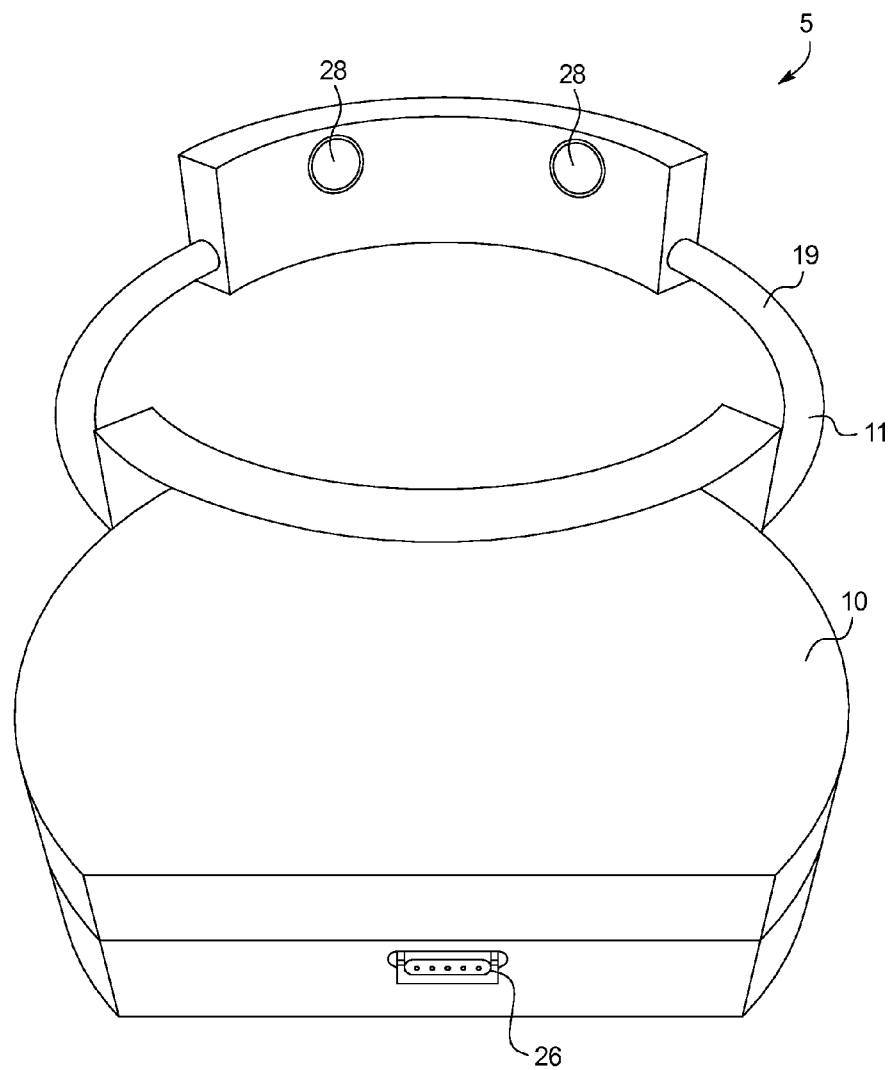
FIG. 4B is a top view of an embodiment of the device disclosed herein, wherein the interior of the housing is exposed.

As shown in FIGS. 2A-2B, the housing 10 may have a removable section 25 to allow for the replacement of the battery/batteries 21. If the batteries 21 are rechargeable, then instead of having the removable section 25, the housing 10 may have a port 26 (e.g., a micro-USB charging port or similar charging port) that allows a charging cable to be connected, as shown in FIGS. 4A-4B.

As shown in FIG. 3A, the housing 10 may include one or more printed circuit boards 27 that may contain many of the electronics necessary to accomplish the described functions. The printed circuit board(s) 27 may be laid out in a way to minimize size and weight, while also enabling the proper placement of the diagnostic sensors 6 to give the most accurate readings possible.

The device 5 may include a power supply module 24 that includes a small battery 21, or multiple batteries 21 combined in either series, parallel or both to accommodate the required voltage and current draw of the device and all its related electrical components. The power supply 24 may include any type of battery/batteries 21 (LiPo, Li-ion, LiFePO4, NiCd, NiMH, etc.) in a configuration that produces the proper capacity and voltage necessary for operation, as will be recognized by those skilled in the art based on the descriptions provided herein. The accompanying circuitry may include either a linear regulator, switching regulator, or any other type of circuitry used to produce a steady, accurate voltage, necessary for obtaining accurate and useful data from the biometric sensors, powering the microcontroller 17, wireless module 18, and sensors 6, and operating the adjustable ring 11.

The device 5 may also include a wireless module 18 that includes a communication module which allows the device 5 to connect wirelessly to an external device, such as a smartphone, tablet, or other computer, to transfer the data from the sensors to the supporting software applications residing on the external device. The wireless module 18 may use any available means of transmitting data without the use of wires, protocols such as BT, WiFi, ANT+, or any other data-transmitting technology that may become available in the future.

As discussed above, the system and device 5 disclosed herein may include a variety of diagnostic sensors 6, which we will turn to now. However, it is contemplated that any number of sensors 6 may be included in the system and device 5, and, thus, the device 5 is not limited to the specific sensors 6 discussed below.

The at least one diagnostic sensor 6 may include an accelerometer 12 to report movements in three dimensions. This can be used to determine wake/sleep mode in order to save battery life, and also to log movement for linking certain activities to penile diagnostics. The accelerometer 12 may be used to monitor the general motion of the device 5, and, thereby, the motion of the penis attached to the device 5.

The device 5 may include an inertial measurement unit (IMU) device that measures velocity, orientation, and gravitational forces by using a combination of accelerometers, gyroscopes, and magnetometers. The IMU may be configured to measure a current rate of acceleration using one or more accelerometers (linear and angular) 12, and changes in rotational attributes like pitch, roll, and yaw using a gyroscope.

The diagnostic sensor 6 may include a temperature sensor 13 that reports changes in skin temperature in various locations. Various types of temperature sensors 13 may be suitable to measure temperature data.

In another example, the diagnostic sensor 6 may include a pulse oximeter 16, an infrared light emitting diode (LED) 16a, and a red LED 16b used to transmit light to the skin. The reflected light is detected by a photo-transistor and the resulting signal can be used to calculate pulse, and oxygen saturation in the blood. In addition, the accelerometer 12 may also be used to modify and/or stabilize the data from the pulse oximeter 16 in cases where activity or motion disrupts the readings.

As mentioned above, an array of disposable, flexible, unobtrusive, bend sensors 22 may be embedded in a condom-like attachment 23. In the embodiment shown in FIG. 7, the attachment 23 is disposable and detachable, and measures the specific bending in the penis along the shaft. Multiple bend sensors 22 may be arranged in zones along the shaft to measure the specific location of bending.

In yet another example, the diagnostic sensor 6 may include a sound-speed ultrasonic transmitter 14a and sound-speed ultrasonic receiver 14b paired to measure the speed of sound through the penis, which will vary based on rigidity. The basic principle behind these sensors is that sound will travel faster through a denser material than a less dense one (i.e., sound travels much faster through solids than it does air and/or gas and most liquids since particles are packed more closely together). Based on the results from the circumference gauge 19, the diameter value recorded can be used as the distance between the sound-speed ultrasonic transducer 14a and the sound-speed ultrasonic receiver 14b. Sending a sound wave of a certain frequency across the diameter of the penis shaft, the elapsed time will be measured and used to determine the speed of sound. During a flaccid state, sound will travel slower than during the erect state, thus giving a numerical value as to the density and/or rigidity over the course of study.

Alternatively or in addition to the sound-speed ultrasonic transmitter 14a and the sound-speed ultrasonic receiver 14b, a color Doppler ultrasonic transducer 15a and a Doppler ultrasonic receiver 15b may be paired to transmit high frequency ultrasound at varying frequencies and measure the amount of time and frequency of the return echoes. After some signal processing, the received data can be used to provide an assessment of relative blood flow into the cavernosal arteries and out of the sinusoids.

The present disclosure also provides a system 5 for measuring sexual function comprising a device 5, wherein the device 5 includes an adjustable ring 11 forming an opening to receive a penis, and at least one diagnostic sensor 6 positioned on an inner surface 7 of the adjustable ring 11, wherein the adjustable ring 11 automatically couples the diagnostic sensor 6 to the penis throughout a range of ring diameters. The system 5 further includes a microcontroller 17 in communication with the at least one diagnostic sensor 6, wherein the at least one diagnostic sensor 6 measures data during sexual activity and communicates the data to the microcontroller 17. The system 5 also includes an application 30 in communication with the microcontroller 17, wherein the application 30 is configured to analyze the data received from the microcontroller 17.

Figure 8:
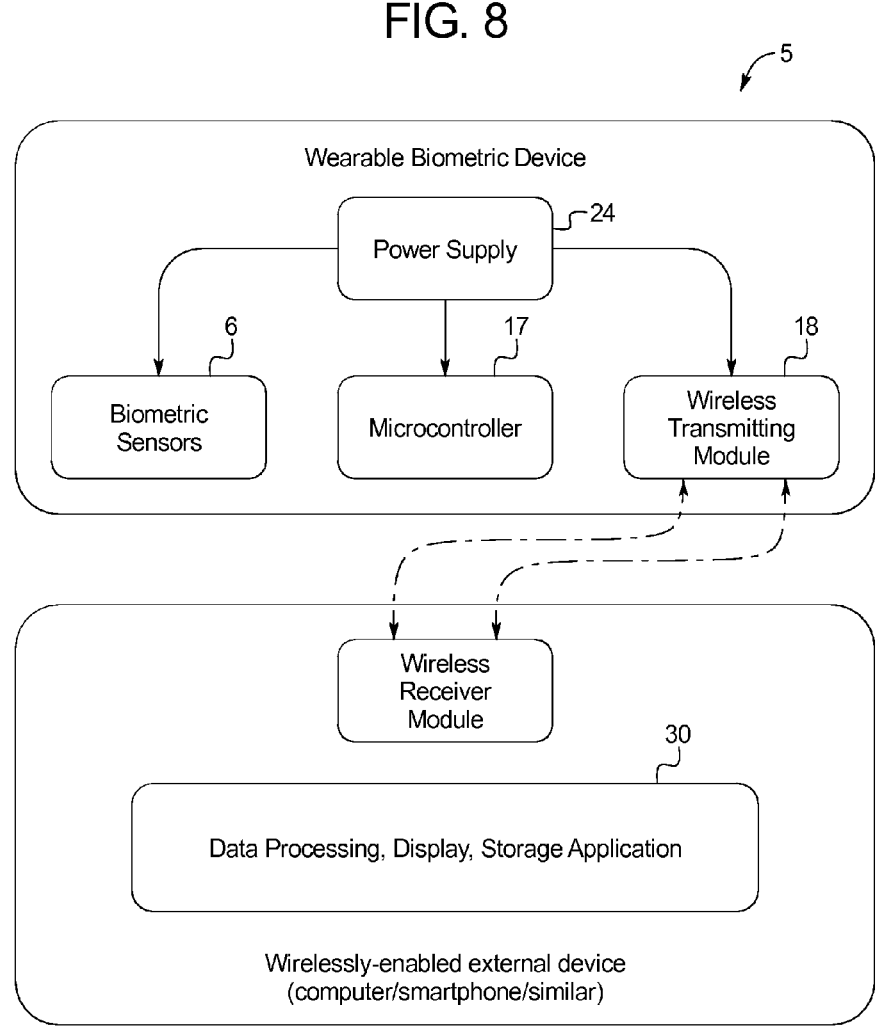
FIG. 8 is a schematic of an embodiment of the system disclosed herein.

The application 30 may run on a user's wireless-enabled and Internet connected device, such as a smart phone, tablet computer, laptop computer, or desktop computer, as shown in FIG. 8. The application 30 accepts the incoming data from the device's wireless module 18 and processes it for use in a number of ways.

Data processing methods of the application 30 may ensure the validity and reliability of the data streams and amalgamate the data to generate an erectile index of 0-100. The erectile index may be used to rate the rigidity and quality of the erection along with other biological parameters, based on an algorithm factoring in the measurements and data provided by the device 5.

Along with producing an erectile index, the application 30 may also display the incoming data in a number of ways including: real-time graphs display data streams such as the elapsed erectile time, penile skin temperature, average direction of blood flow through the corporal arteries or clitoral arteries and venous plexuses, pulse oximetry data, and movement data, such as the number of pelvic thrusts.

Other means of graphical display of relevant data may be included. For example, a color change in the display may signal when the erection reaches maximal rigidity. Once the erection starts to decrease in rigidity, the color may change again and the device may give the user a choice of modulating his or her erection using an automated adjusting ring 11 to maximize its duration and length through intermittent compression of the device 5. Once the individual reaches climax, the rhythmic contractions of the periurethral muscles will be noted by the processing software and this may be denoted by another color change on the display. The device 5 may also measure time until orgasm.

A function may also be included within the application 30 to enable a man or woman's partner to visualize their penile or clitoral diagnostics. Should a couple each be wearing one of the devices 5, the application 30 may enable instantaneous feedback for maximizing the sexual enjoyment of both partners. After the act of coitus, the display page would log, characterize, and display any and/or all of the metrics captured by the device 5. Further, the application 30 may also generate a log of the raw data, along with all other processed data, giving the user the ability to track and compare his performances with past data.

The application 30 may also include an internet-based counterpart, allowing the user to upload the data in real-time to a secure and protected database. Before uploading, the data may preferably be de-identified to protect privacy, with each individual identified only by a unique signature (such as a 15-digit alpha-numeric device signature), if at all. The data may be stored on external servers, which will house the data for future research and ongoing analytics. The user may also have the ability to share the data with others of his or her choosing, such as partners, medical professionals for remote diagnosis, or for anonymous data/test collection.

This application 30 may also have the ability to modulate the device's 5 adjustable ring 11 in real-time to maximize the rigidity and duration of a penile or clitoral erection and to sync with a partner's device 5 to provide real-time sexual feedback to both users wearing devices 5 during coitus or stimulating themselves in remote locations.

It should be noted that various changes and modifications to the embodiments described herein will be apparent to those skilled in the art. Such changes and modifications may be made without departing from the spirit and scope of the present invention and without diminishing its attendant advantages. For example, various embodiments of the method and portable electronic device may be provided based on various combinations of the features and functions from the subject matter provided herein.

I claim:

1. A device for measuring sexual function comprising:
an adjustable ring forming an opening to receive a penis;
at least one diagnostic sensor positioned on an inner surface of the adjustable ring, wherein the ring automatically couples the diagnostic sensor to the penis throughout a range of ring diameters, wherein the at least one diagnostic sensor includes a temperature sensor configured to measure penile temperature data; and
a microcontroller in communication with the at least one diagnostic sensor,
wherein the at least one diagnostic sensor measures data during sexual activity and communicates the data and the penile temperature data to the microcontroller.

2. The device of claim 1 wherein at least a portion of the adjustable ring is an elastic circumferential gauge, wherein the microcontroller is configured to receive data from the elastic circumferential gauge.

3. The device of claim 1 further comprising a power supply module.

4. The device of claim 1 further comprising a wireless communication module.

5. The device of claim 1 wherein the data includes blood flow data, rigidity data, temperature data, 3-axis acceleration data, or combinations thereof.

6. The device of claim 1 wherein the at least one diagnostic sensor includes a blood flow sensor configured to measure blood flow data.

7. The device of claim 6 wherein the blood flow sensor includes an ultrasound transducer.

8. The device of claim 1 wherein the at least one diagnostic sensor includes a rigidity sensor configured to measure penile rigidity data, wherein the rigidity sensor includes an ultrasound transducer.

9. The device of claim 1 wherein the device further includes an accelerometer, wherein the microcontroller is configured to receive 3-axis acceleration data from the accelerometer.

10. The device of claim 1 wherein the device includes a pulse oximeter sensor configured to measure oxygenation data, wherein the microcontroller is configured to receive oxygenation data from the pulse oximeter sensor.

11. The device of claim 1 wherein the device further includes a strain gauge used to determine circumferential data.

12. The device of claim 1 wherein the device is configured to be worn by a user during sexual activity.

13. The device of claim 1 wherein the microcontroller adjusts the diameter of the adjustable ring based on received data.

14. A system for measuring sexual function comprising:
a device comprising:
an adjustable ring forming an opening to receive a penis, and at least one diagnostic sensor positioned on an inner surface of the adjustable ring, wherein the adjustable ring automatically couples the diagnostic sensor to the penis throughout a range of ring diameters, and wherein the at least one diagnostic sensor includes an accelerometer for monitoring movement of the penis;
a microcontroller in communication with the at least one diagnostic sensor, wherein the at least one diagnostic sensor measures data during sexual activity and communicates the data to the microcontroller; and
an application in communication with the microcontroller, wherein the application is configured to display the data received from the microcontrollers;
wherein the microcontroller is configured to receive 3-axis acceleration data from the accelerometer.

15. The system of claim 14 wherein the at least one diagnostic sensor includes a blood flow sensor including an ultrasound transducer.

16. The system of claim 14 wherein the at least one diagnostic sensor includes a rigidity sensor including an ultrasound transducer.

17. The system of claim 14 wherein the device further includes a strain gauge used to determine circumferential data.

18. The system of claim 14 wherein the microcontroller, in response to the data, is configured to adjust a diameter of the ring to enable a user to maintain an erection during sexual activity.

* * * * *